United States Patent
Hehrlein

(10) Patent No.: US 10,426,511 B2
(45) Date of Patent: Oct. 1, 2019

(54) DEVICE FOR DETACHING PARIETAL THROMBI FROM A BLOOD VESSEL

(71) Applicant: UNIVERSITÄTSKLINIKUM FREIBURG, Freiburg (DE)

(72) Inventor: Christoph Hehrlein, Freiburg (DE)

(73) Assignee: UNIVERSITÄTSKLINIKUM FREIBURG, Freiburg (DE)

( * ) Notice: Subject to any disclaimer, the term of this patent is extended or adjusted under 35 U.S.C. 154(b) by 405 days.

(21) Appl. No.: 14/440,847

(22) PCT Filed: Oct. 21, 2013

(86) PCT No.: PCT/EP2013/003166
§ 371 (c)(1),
(2) Date: May 5, 2015

(87) PCT Pub. No.: WO2014/067631
PCT Pub. Date: May 8, 2014

(65) Prior Publication Data
US 2015/0289902 A1   Oct. 15, 2015

(30) Foreign Application Priority Data
Nov. 5, 2012 (DE) .......... 10 2012 021 729

(51) Int. Cl.
*A61B 17/22* (2006.01)
*A61B 17/3207* (2006.01)

(52) U.S. Cl.
CPC ........... *A61B 17/320725* (2013.01); *A61B 17/22031* (2013.01); *A61B 17/22032* (2013.01);
(Continued)

(58) Field of Classification Search
CPC ........ A61B 17/22031; A61B 17/22032; A61B 17/320725; A61B 2017/22047; A61B 2017/22048; A61B 2017/22051
See application file for complete search history.

(56) References Cited

U.S. PATENT DOCUMENTS 5,456,667 A * 10/1995 Ham ................. A61M 25/0074
                                                        604/104
5,556,413 A    9/1996 Lam
(Continued)

FOREIGN PATENT DOCUMENTS

DE    102009017050 A1    11/2010
DE    102011120004 B3    3/2013
(Continued)

OTHER PUBLICATIONS

International Search Report for International Application No. PCT/EP2013/003166 dated May 12, 2013.

*Primary Examiner* — Robert A Lynch
(74) *Attorney, Agent, or Firm* — Fitch, Even, Tabin & Flannery LLP

(57) ABSTRACT

A device for detaching parietal thrombi from a bodily vessel is described having a catheter including at least one catheter section with a catheter wall with at least one wall opening which passes completely through the catheter wall. The catheter wall along the least one catheter section is made of a resiliently deformable material in which the at least one wall opening includes a separating helical gap wound around the catheter wall at least in parts along the catheter section. A fixing device permits releasable fixing of the catheter on a bodily vessel so that the catheter can be converted, exclusively by an external mechanical constraint in the form of a torque acting torsionally on the catheter, (Continued)

from a state of smaller catheter outer diameter to a state of larger catheter outer diameter.

14 Claims, 3 Drawing Sheets

(52) U.S. Cl.
CPC ............... *A61B 2017/22034* (2013.01); *A61B 2017/22041* (2013.01); *A61B 2017/22045* (2013.01); *A61B 2017/22069* (2013.01); *A61B 2017/22079* (2013.01)

(56) References Cited

U.S. PATENT DOCUMENTS

| | | | |
|---|---|---|---|
| 5,954,745 A * | 9/1999 | Gertler | A61F 2/013 606/159 |
| 6,027,516 A * | 2/2000 | Kolobow | A61F 2/88 623/1.11 |
| 2001/0041899 A1 | 11/2001 | Foster | |
| 2003/0236531 A1 | 12/2003 | Couvillon, Jr. | |
| 2005/0000430 A1 | 1/2005 | Jang et al. | |
| 2006/0064073 A1 | 3/2006 | Schonholz et al. | |
| 2006/0074441 A1 | 4/2006 | McGuckin, Jr. et al. | |
| 2006/0253145 A1 | 11/2006 | Lucas | |
| 2007/0208361 A1 | 9/2007 | Okushi et al. | |
| 2008/0300532 A1 | 12/2008 | Bonnette et al. | |
| 2009/0270800 A1 | 10/2009 | Spurchise et al. | |
| 2010/0087844 A1 | 4/2010 | Fischer, Jr. | |
| 2010/0125239 A1 | 5/2010 | Perry et al. | |
| 2010/0132748 A1 | 6/2010 | Kessler et al. | |
| 2011/0040314 A1 | 2/2011 | McGuckin, Jr. et al. | |
| 2011/0166637 A1 | 7/2011 | Irwin et al. | |
| 2012/0071910 A1* | 3/2012 | Anderson | A61M 25/005 606/191 |

FOREIGN PATENT DOCUMENTS

| | | |
|---|---|---|
| WO | 0007657 A1 | 2/2000 |
| WO | 0156644 A1 | 8/2001 |
| WO | 2005018728 A2 | 3/2005 |

* cited by examiner

DEVICE FOR DETACHING PARIETAL THROMBI FROM A BLOOD VESSEL

CROSS REFERENCE TO RELATED APPLICATIONS

Reference is made to PCT Application No. PCT/EP2013/003166, filed on Oct. 21, 2013, and German Application No. 10 2012 021 729.3, filed Nov. 11, 2013, which applications are incorporated herein by reference in their entirety.

BACKGROUND OF THE INVENTION

Field of the Invention

The invention relates to a device for detaching parietal thrombi from a bodily vessel. The device has a catheter having a catheter longitudinal dimension including at least one catheter section having an outer catheter wall diameter which is variable and the catheter wall has at least one wall opening passing completely through the catheter wall.

Description of the Prior Art

A large number of catheter-based, medical instruments that are used for gentle ablation of deposits on vessel inner walls caused by aging or disease are known for interventional treatment of vessels which have been narrowed by parietal thrombi and through which bodily fluids flow. The medical instruments, often referred to as thrombectomy catheter systems, each have a catheter tip suitable for tissue ablation, by which the ablated thrombus material is disposed of outside the body, usually in a manner assisted by a vacuum prevailing within the catheter lumen.

To this end, a mechanical thrombectomy catheter system having a multi-lumen catheter, which can be positioned with the aid of a guide and positioning wire relative to a thrombosis, which is initially pre-treated with a lysis solution via a rinsing channel is disclosed in US published application 2010/0087844 A1. A scraping tool formed in the manner of a basket exits the catheter at the distal end via an instrument channel running along the catheter. Fragments of the surrounding thrombus material are removed by an axial movement to and from. The separate thrombus material fragments can be collected and brought outside the body via a further aspiration channel provided along the catheter.

In contrast to the axially movable, basket-like scraping tool, as explained above, US published application 2006/0074441 A1 and 2011/0040314 A1 are thrombus material removal tools formed to have a wire, each have a tool tip formed in the manner of a wire, a sinusoidal wire form which, with rotation about the wire having longitudinal axis, has the effect of a spindle-shaped cutting structure and, upon contact with thrombus material adhering to the vessel wall, can comminute the material as a result of rotary shear forces and can remove the comminute material. Detached thrombus material fragments in this case are brought outside the body using a suitably placed aspiration catheter.

A further thrombus material ablation tool is described in US 2006/0064073 A1, which describes a catheter tool which is guided through an aspiration catheter. On the distal catheter region, an ablation tool is mounted that can be spread apart in a wedge-like manner radially relative to the catheter axis. The ablation tool fragments intravascular thrombus material on account of a rotary movement about the catheter axis. Due to the tool limbs being oriented as a wedge and due to the suction effect prevailing by the aspiration catheter, the fragmented thrombosis material particles pass in a proximal direction from the tool catheter tip into the aspiration catheter.

An advantageous addition to the mechanical thrombectomy catheter system described above is described in US published application 2006/0253145 A1, in which an inflatable balloon is provided at the distal end of the catheter tool. The balloon on the one hand centers the tool catheter axially within the vessel relative to the thrombus material to be removed, which ensures that no fragments of thrombus material that are separated from the vessel wall can pass distally from the fan-shaped, expanded and rotating removal tool into the bloodstream in an uncontrolled manner.

US Published Application No. 2007/0208361 A1 describes an atherectomy catheter system that has an aspiration catheter beyond which a radially expandable stent graft and also a centrally guided needle protrude distally, which are mounted jointly in a co-rotating manner which punctures, separates and comminutes thrombus material in a manner comparable to a drill head when advanced in the distal direction along a stenosed bodily vessel. The fragmented thrombus material pieces are brought outside the body via the aspiration catheter.

A further method for the local separation of stenosed tissue regions is provided by catheter systems having cutting tools. A catheter at the distal peripheral outer region at which individual inflatable bodies are arranged in the peripherally to individually position the axial placement of the distal catheter tip relative to a vessel to be treated can be inferred from US Published Application No. 2009/0270800 A1. Furthermore, a cutting blade, that can be guided via the catheter tip, is provided within the catheter. The cutting blade separates thrombus material from the vessel wall and the separated thrombus material pieces then pass through an aspiration channel along the catheter arrangement.

A comparable catheter arrangement is described in WO 2010/132748 A1, which also provides a cutting tool that is mounted in a guidable manner both axially by a radially splayable catheter tip and via an opening provided laterally along the catheter arrangement.

A thrombectomy catheter through which fluid flows is described in US Published Application No. 2008/0300532 A1, which is positioned by a guide wire extending along a stenosed vessel site. The catheter has, along a distal catheter section, at least two openings oriented transversely to the catheter longitudinal extent. One opening serves as a fluid discharge from which a fluid flow exits transversely to the vessel longitudinal extension onto the thrombus material to be removed. The material is detached locally from the vessel inner wall, thus forming very small thrombus material fragments. The detached thrombus fragments pass via the second opening into the interior of the catheter, along the length of which the fluid flow containing thrombus material is brought outside the body.

Lastly, DE 10 2009 017 050 A1 describes a device for detaching concretions from a bodily vessel using a catheter, by which a tool catheter can be positioned relative to a thrombosis to be removed. The tool catheter has a stent-shaped catcher element, which spontaneously expands radially once removed distally from the catheter. The catcher element has entry openings formed as slots, through which the concretion material to be removed, in particular thrombi, flows to the interior of the catcher element. As a result of axial and also rotary movements of the tool catheter, the thrombus material protruding through the entry openings into the interior of the catcher element is detached on account of shear forces occurring and can be brought outside the body in the form of fragmented individual pieces by application of a vacuum applied within the tool catheter. In order to remove the catheter arrangement from the vessel, the catcher element is drawn in the proximal direction by radially acting compressive forces into the channel and is removed from the body in this compressed state.

All of the above known solutions constitute catheter designs that are technically complex in part, of which the operative handling places high demands on the operator, especially since the tools for local intravasal removal of parietal thrombi usually have sharp edges and must be operated with great care in order to avoid causing damage to vessel walls.

The devices disclosed in U.S. Pat. No. 7,063,671 B2 for removing samples or for removing polyps from a body of a patient have actuators made of electroactive polymer material, which can be contracted and expanded by electrical stimulation. Openings in the device can be widened by appropriate actuation of the actuators to grasp a sample or the polyp.

US Published Application No. 2010/0125239 A1 explains, as an alternative to cutting, ablating or vaporising stenosis treatment methods, a catheter having an inflatable balloon, with which medicines can be applied at a specific site within a lumen, for example an artery. The catheter thus has a balloon which is surrounded by a porous membrane. A medicine is located in the space between balloon and membrane. By activating electrodes located on the membrane and as a result of the thermal energy supplied during this process, the membrane pores open and molecules of a medicine are pushed by the pressure produced by the balloon through the membrane pores to the tissue to be treated. The balloon also causes a radial expansion, under which the catheter comes into contact with the surrounding tissue.

A catheter device for detaching parietal thrombi that is more economical compared with the above, known catheter solutions and that is more easily operated by the operator can be found in German patent application DE 10 2011 120 004.9. The device utilizes the resilient properties of a tubular catheter consisting of an elastomer, in the catheter wall having wall openings passing completely through the catheter wall. The wall openings, with the aid of a displacement body insertable along the catheter, can be converted by radial extension of the tubular catheter into an expanded opening state. Parietal thrombus material infiltrates the region of the expanded catheter wall openings with suitable intravascular positioning of the catheter and, following removal of the displacement body from the catheter and an accompanying resilient return of the expanded catheter into the original state thereof, is fixedly clamped within the catheter wall openings made smaller, thus producing shear forces, and is then removed by extracorporeal removal of the catheter.

US Published Application No. 2005/0080430 A1 discloses a catheter having an expandable, distal end, having a medical device located in front of the catheter end in a body lumen. The medical device has a larger diameter than the catheter and can be removed or brought to another location within the body. The end of the catheter has slots, which at least partially do not run parallel to the longitudinal extension of the catheter. The slotted region is held together by a ductile elastomer layer arranged on the outer side.

SUMMARY OF THE INVENTION

The invention provides a device for detaching parietal thrombi from a bodily vessel, which is as simple as possible, economical and easily operabled by the operator and which largely prevents vessel wall damage. In addition, parietal thrombus material is to be removed from the vessel wall reliably and efficiently with as little residue as possible. The thrombus fragments which are separated from the vessel wall are to be brought reliably outside the body.

Proceeding from the German Patent Application No. DE 10 2011 120 004.9, the invention similarly utilizes the resilient properties and the associated resilience restoring forces of a catheter section, a resiliently deformable material for receiving and also separating parietal thrombus material from a bodily vessel, while eliminating the need for a displacement body as in the prior art explained above. The new catheter device of the invention has a simpler design and can be handled more easily and also can be produced more economically than the prior art.

The new device in accordance with the invention detaches parietal thrombi from a bodily vessel. The device has a catheter, at least one catheter section extending longitudinally along the catheter associated catheter wall including at least one wall opening which passes completely through the catheter wall transversely to the catheter longitudinal extent. The catheter or the least one catheter section is made of a resiliently deformable material. The at least one wall opening includes a separating gap winding which is helically coiled around the catheter wall at least in parts along the catheter section. The separating gap, which preferably winds helically over the entire axial extent of the catheter section, is preferably formed as a cut passing completely through the catheter wall, so that no catheter wall material is removed in order to form the cut. The catheter wall faces run along the helically winding separating gap and face one another in a planar manner.

The catheter has, in the distal direction from the at least one wall opening formed with helical winding separating gap, a fixing means which permits temporary releasable fixing the catheter on or within a bodily vessel. The fixing device is formed in particular in such a way that the catheter can be anchored or can be fixed intracorporeally so as to be secured against rotation about its catheter longitudinal axis where possible.

In a preferred embodiment, the fixing means is a dilatable balloon, which is fixedly mounted preferably on the distal catheter tip or at least in the distal direction from the at least one helically winding separating gap along the catheter and can be dilated via a lumen guided within the catheter by filling with a suitable gaseous or liquid medium. Alternatively, to a fixed mounting of a balloon on the catheter, it is also possible to provide a balloon catheter that can be handled separately from the catheter and to slide the balloon through the inner lumen of the catheter in the distal direction until the balloon is positioned at the distal end of the catheter or protrudes therebeyond in the distal direction. As a result of appropriate inflation, the balloon can securely fix the catheter within a vessel distally, such that the catheter is fixed at one end in particular to secure the catheter against rotation relative to the catheter longitudinal axis.

Of course, it is possible and conceivable to provide the fixing of the catheter in another way, for example in the form of anchoring structures, which are dynamically extendable or unfoldable from the catheter at the distal region of the catheter. Anchoring structures of this type have long been known in the art and therefore do not require a detailed description.

The catheter according to the invention as explained above is positioned, for the purposes of gentle intravascular ablation of parietal thrombus material within a bodily vessel so that the catheter section having the at least one helically wound separating gap is positioned directly along an intravasal, parietal thrombus deposit. In this position, the catheter must be fixed preferably at the distal end with the aid of the fixing means so that the catheter is fixed axially along the vessel, but in particular in a manner secured against rotation. In this state, an external mechanical constraint must be exerted via an extracorporeally accessible catheter section onto the catheter which is a torque acting torsionally along the catheter, such that the direction of rotation forming the basis of the torque is oriented against the winding direction associated with the helically winding separating gap. The torque can be produced in metered form by manually twisting the catheter or with the aid of a rotary drive, driven by electric motor, mounted suitably on the proximal end of the catheter.

As a result of the fixing of the catheter at the distal end with the fixing means, which takes up the torque at the end, the torque acting along the catheter can convert the catheter section, along which the at least one helically wound separating gap extends, from a state with a relatively small catheter outer diameter into a state with a relatively larger catheter outer uniform diameter by way of a resilient change in shape of the catheter wall. The helically winding separating gap widens from a closed gap state to an opened gap state upon the application of the torque. Due to the radial widening of the catheter section, the catheter outer wall is pressed against parietal thrombi, which projects at least in part into the space of the opened separating gap.

Once the external mechanical constraint has been removed, the torque acting torsionally on the catheter is eliminated and the catheter spontaneously resumes a state with the relatively smaller catheter outer diameter resulting from resilient restoring forces inherent to the material. The forcibly opened separating gap is converted into the initial, closed gap state. Due to the width reduction, thrombus material projecting within the separating gap is positively clamped and ultimately sheared off from other parietal residual material.

The thrombus material advantageously can be sheared off in an assisted manner in that a torque oriented in the winding direction of the helically winding separating gap is introduced along the catheter from the proximal end. The sectional faces of the gap defined by the helically winding separating gap on either side are pressed against one another with an additional force and therefore the shearing-off forces directed onto the thrombus material can be increased.

For the purposes of the most complete possible grasping, ablation and lastly extracorporeal removal of parietal thrombus material from a bodily vessel, it is advantageous to apply a vacuum along the catheter along the lumen enclosed by the catheter and in particular along the catheter section provided with the at least one helically winding separating gap. The applied vacuum makes possible aspiration of the parietal thrombus material through the separating gap when the gap is in the opened state into the interior of the catheter section, and to also reliably store said material there in the re-closed state of the catheter. For this purpose, in one variant, the catheter has at the proximal catheter end thereof a connection structure for the fluid-tight connection to a suitable vacuum source or aspiration source.

It is of course possible to provide two, three or more helically winding separating gaps within the catheter wall along the catheter section, which is preferably made of a resiliently deformable elastomer and designed in a cylindrical or tubular manner which comprises an inner catheter lumen and each of the separating gaps having an identically oriented winding direction. The helicity of the at least one separating gap is preferably designed with a uniformly constant pitch, which preferably extends over the entire length of the catheter section. Nevertheless, it is possible to provide at least two axial regions along the catheter section, within each of which axial regions the helically winding separating gap has a different pitch. If it is necessary by way of example to detach the greatest possible quantities of parietal thrombus material from a vessel wall region, a catheter designed in accordance with the invention is suitable, having at least one helically winding separating gap with the pitch being selected to be minimal, that is, as many turns as possible are provided within an axial region along the catheter section.

A further advantageous embodiment has, along the catheter section and in addition to the least one helically winding separating gap, at least one wall opening which passes completely through the catheter wall, which in contrast to the design of the least one helically winding separating gap is formed by a material cutout from the catheter wall and preferably has a maximum opening width from 0.1 to 20 mm. The at least one further wall opening retains its opening geometry, which is preferably round, oval, n-cornered, or has an opening shape deviating herefrom, largely in an unaltered manner, even in the case of an above-explained change in shape of the catheter caused by a torque acting thereon.

The at least one further wall opening serves as an aspiration opening in the case of a vacuum applied within the lumen enclosed by the catheter. As a result of the vacuum, parietal thrombus material can be sucked in, primarily in the above-described closed catheter state, during which the catheter adopts during an intracorporeal insertion and positioning and also a subsequent extracorporeal removal.

Both the process of ablation of parietal thrombus material by the at least one helically winding separating gap and also by the wall openings to be provided additionally within the catheter wall along the catheter section can be assisted in a preferred further embodiment of the catheter according to the invention by axial and/or radial movements of the catheter relative to the stenosed vessel site. The relative movements being performed are either manual by the operator or can be assisted with the aid of a vibrator unit suitably provided proximally on the catheter.

In principle, the catheter system according to the invention does not have any cutting tools that could potentially damage the healthy vessel wall and that are to be guided intravasally separately from the catheter, as is the case in the relevant prior art. Rather, the catheter system according to the invention enables a gentle and completely damage-free thrombus material ablation from the vessel inner wall, especially because, when the healthy vessel inner wall is reached by the catheter, the healthy vessel wall material bears against the catheter outer wall parallel thereto and cannot reach into the widened separating gap. The catheter provided with at least one lateral separating gap opening and where appropriate with additional wall openings thus makes it possible to remove merely tissue material adhering to the vessel wall which is material jutting out beyond the vessel wall surface.

In order to completely eliminate parietal thrombus material, it is usually necessary to position the catheter relative to the thrombus material present intravasally and to perform the above-described separation process a number of times in succession. It is indeed possible to withdraw the catheter in the proximal direction after each individual tissue separation by a working catheter also introduced intracorporeally and to clean the catheter accordingly of the separated tissue material extracorporeally in order to reposition the catheter intracorporeally. However, it is advantageous in cases in which larger quantities of thrombus material are to be removed at a stenosis to attach a vacuum source to the catheter at the proximal end, via which the separated thrombus material can be brought outside the body within the catheter in the proximal direction.

The catheter wall in particular in the region of the catheter section, is made of a biocompatible elastomer, which is made of at least one material from the following materials: poly(methyl methacrylate) (PMMA), polytetrafluoroethylene (PTFE), polyurethanes, polyether urethanes, silicone polyether urethanes, silicone polyurethanes, silicone polycarbonate urethanes, polyolefin elastomers, polyisobutylenes, fluorosilicones, polyvinyl chloride (PVC), polydimethylsiloxane (PDMS), polylactides, polyethylene, polybutylmethacrylate, polyacrylamide, polyacrylonitriles, polyamides, polyetheramides, polyethylene amine, polyimides, polycarbonates, polycarbonate urethanes, polyvinyl ketones, polyvinyl halides, polyvinylidene halides, polyvinyl ether, polyisobutylenes, polyvinyl aromates, polyvinyl ester, polyvinyl pyrrolidones, polyoxymethylenes, polytetramethylene oxide, nylon or polyester.

The above materials enable a simple and economical production of the catheter according to the invention in that at least one helically winding separating gap in the form of an incision along the catheter section is formed with the use of conventional cutting methods. Due to the cutting process, the catheter does not experience any material removal or virtually no material removal, such that two separating gap sectional faces bearing directly against one another along the catheter section are formed and are defined respectively by a sharp cutting edge arranged radially inwardly and outwardly of the catheter. The cutting edges complete separation of the thrombus material to be ablated from the vessel inner wall.

BRIEF DESCRIPTION OF THE DRAWINGS

The invention will be described by way of example hereinafter without limitation of the general inventive concept on the basis of exemplary embodiments with reference to the drawings, in which.

DETAILED DESCRIPTION OF THE INVENTION

Figure 1A:
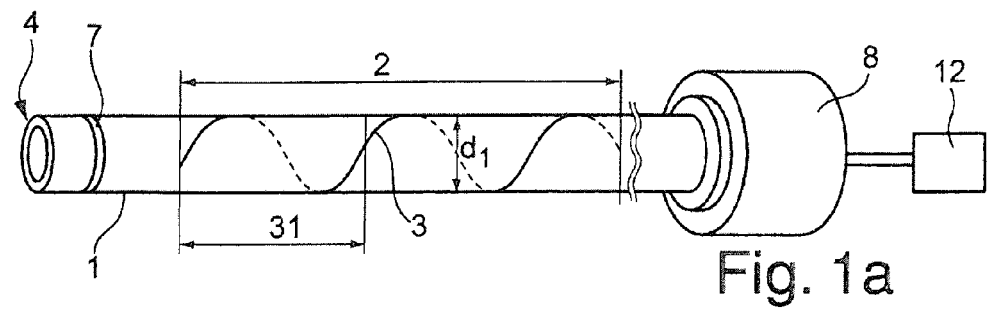
FIGS. 1a and b show schematic illustrations of a catheter formed in accordance with the invention a) in a state free from external forces and b) in a state with torque acting along the catheter.

FIG. 1a shows, in a highly schematic manner, a catheter 1 formed in accordance with the invention, which is cylindrical or tubular with the catheter wall being made of a biocompatible resilient elastomer. At least one catheter section 2 is provided along the catheter 1, in which the Catheter section has a helically winding separating gap 3 of constant pitch formed therein. The separating gap is produced with a non-material-removing separation procedure, which preferably is made by a cutting procedure, in the form of an incision which passes completely through the catheter wall. The catheter section 2 does not experience any externally visually perceptible surface disruption on account of the helically winding separating gap 3. The separating gap 3 is designed as a helical incision having a closed form, which does not have a gap opening. In the case illustrated in FIG. 1a, the helical separating gap 3 has two and a half turns 31 with each having constant pitch.

Figure 1B:
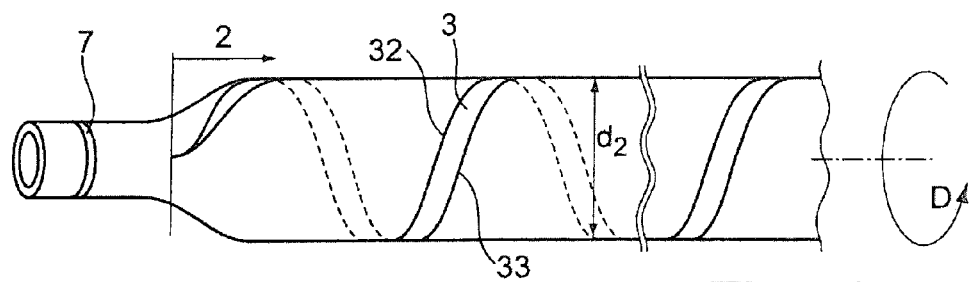

If the catheter illustrated in FIG. 1a is provided with at least one helically winding separating gap 3 which is fixed at the distal catheter tip 4 thereof, upon addition of a torque D applied at the proximal end to the catheter 1 and the direction of rotation of the torque is oriented opposite the winding direction of the helically winding separating gap 3 formed in the catheter 1, the separating gap 3 opens. When open, the opposite sectional faces 32 and 33 of the separating gap 3 are separated from one another with a constant separation when facing each other and include cutting edges at the surface of the sectional faces, as is illustrated in FIG. 1b. At the same time, the catheter outer diameter $d_2$ widens significantly, with $d_2 > d_1$, as can be seen in the illustration according to FIG. 1b compared with FIG. 1a. The torsion-induced gap opening 3 is also accompanied by a longitudinal extension of the catheter 1 in the region of the catheter section 2.

If, by contrast, the torque D reduces to zero, the widened catheter section 2 illustrated in FIG. 1b returns spontaneously into the starting form illustrated in FIG. 1a on account of resilient restoring forces inherent to the material. The opened separating gap 3 thus closes, as is illustrated in FIG. 1a.

Figure 2A:
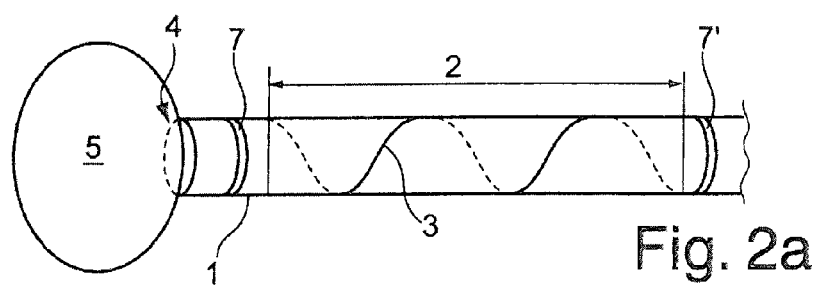
FIGS. 2a-2e show variants for a fixing mechanism.

The above-described mechanism of opening and closing of the separating gap 3 winding helically around the catheter section 2 in the longitudinal direction is suitable for the separation of parietal thrombi within bodily vessels through which blood flows. For an ablation process, it must be ensured that the catheter 1 is positioned intravascularly opposite a thrombus and is fixed at its distal end 4 or at least distally of the catheter section 2 relative to the bodily vessel with the aid of a suitable fixing means. In particular, it must be ensured with regard to the fixing that the catheter 1 is fixed within the hollow vessel in a manner secured against rotation about its longitudinal axis so as to take up the torque necessary in order to open the separating gap and to be supported with respect to the hollow vessel. To this end, a dilatable balloon 5 (see FIG. 2a), which is mounted on the distal end 4 of the catheter 1 and which can be filled with a suitable inflation medium, such as air or a liquid medium, via a supply channel (not illustrated) running accordingly within the lumen of the catheter 1, is preferably used as suitable fixing means. The balloon 5 can be mounted either fixedly on the distal end of the catheter 1 or can be provided separately from the catheter 1 and advanced distally by being slid through the inner lumen of the catheter 1. Radiopaque markings 7 and 7' are formed in or mounted on the catheter 1 distally and proximally adjacently to the catheter section 2, along which the helically winding separating gap 3 is mounted.

Figure 2B:
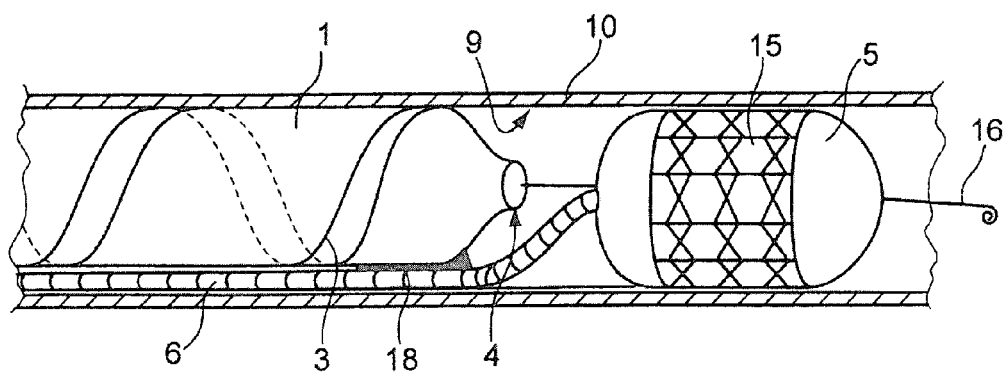

FIG. 2b shows a partial longitudinal section of a catheter 1 placed within a hollow vessel 10. The catheter has a helically winding separating gap 3 along a catheter section 2. The separating gap 3 ends just before the distal end 4 of the catheter 1. At least in this region close to the distal end 4, the catheter 1 is connected to a balloon catheter 6 guided in parallel outside the catheter 1. The connection 18 between the catheter 1 and balloon catheter 6 is designed in such a way that the balloon catheter 6 is fixedly connected at least in the peripheral direction of the catheter 1, as for example by an adhesively or integrally bonded connection.

The balloon catheter 6 surrounds an inner lumen, which can be connected at the proximal end to an inflation arrangement (not illustrated), so that the balloon 5 mounted on the balloon catheter 6 at the distal end can be inflated. The balloon 5 is preferably combined with a net-like, radially expandable stent 15, from which the balloon 5 in the inflated state can press from the inner wall against the bodily vessel inner wall 9 under the application of force to ensure on the one hand that the catheter 1 is held within the bodily vessel 10 in a manner secured against rotation, and on the other hand to allow the stent 15 to widen the vessel locally in situ following corresponding deflation of the balloon 5 and removal in the proximal direction.

When the inflated stent balloon 5/15 is pressed against the vessel inner wall 9 and thus locally closes the vessel, with the balloon inflation typically lasting 1 to 5 minutes, the helically cut catheter section of the catheter 1 is deformed torsionally by application of a torque along the catheter 1 from the proximal catheter end where the separating gap 3 opens. The parietal thrombus is aspirated, by an aspiration vacuum applied at the proximal end along the catheter lumen, on the catheter side of the balloon 5, more specifically via the rotated and therefore opened separating gap 3 of the helically cut catheter section. For the purpose of the intracorporeal navigation of the catheter 1, a guide wire 16 which is guided in an additional lumen running within the catheter lumen also runs in the manner of an "over the wire" configuration. The additional catheter lumen projects distally from the catheter 1 and runs laterally past the dilated balloon 5 or runs therethrough through a corresponding cutout.

It should be noted that the intravasal catheter section, along which the helically winding separating gap 3 is formed, typically has a length of 2-50 cm and is positioned completely intravascularly so that no other tissue material or even air can be aspirated through the helically winding separating gap 3.

Figure 2C:
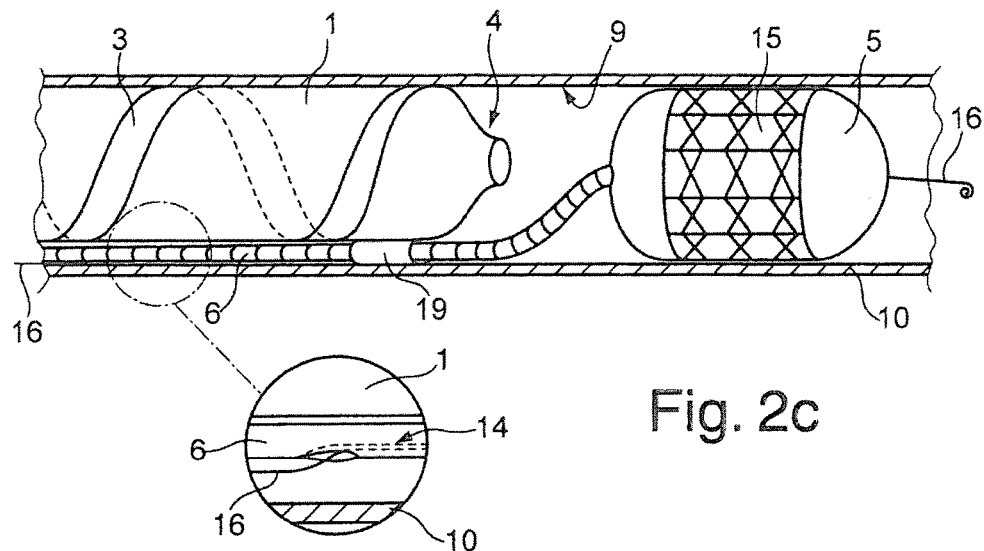

In a further embodiment, which is shown in FIG. 2c, a balloon catheter 6 is guided outside along the catheter 1 in a longitudinally movable manner. In order to connect the balloon catheter 6 in a manner secured against rotation relative to the catheter 1, this has, at its distal end region, an outer, short additional lumen 19, through which the balloon catheter 6 is guided.

With the aid of a guide wire 16, the entire catheter 1 together with the balloon catheter 6 mounted thereon in is a longitudinally movable manner guided intravasally and is positioned relative to a parietal thrombus. The balloon 5 additionally can be advanced in the distal direction relative to the catheter 1 to place the balloon 5 at a distance from the distal end 4 of the catheter 1 and to inflate the balloon in this position. Similar to the exemplary embodiment according to FIG. 2b, the balloon 5 is embodied as a stent balloon 5/15.

The guide wire 16 runs in a monorail configuration, that is largely outside the catheter 1. The guide wire 16 enters a lumen guided along the catheter 1 only at the distal region of the catheter 1, which in the illustrated case runs as an additional lumen 14 within the balloon catheter 6. In this regard see the detailed illustration for FIG. 2c.

Figure 2D:
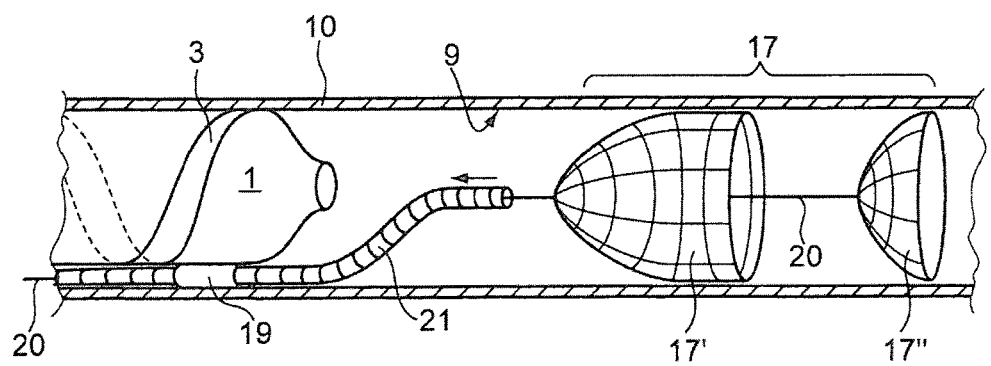

FIG. 2d shows a further embodiment that, instead of the above balloon catheter or stent balloon, a catheter 20 has a fixing means with a self-expanding filter sail arrangement 17, which is guided longitudinally at the distal end 4 of the catheter 1 through an additional lumen 19 mounted fixedly thereon. The filter sail arrangement 17 has two self-expanding filter sails 17' and 17" arranged along a wire 20, which are preferably in a basket and are made of a shape-memory material, which for example may be an Ni—Ti alloy. For the intracorporeal insertion of the entire catheter arrangement, that is the catheter 1 having catheter 21 mounted thereon, both filter sails 17' and 17" are located within the catheter 21 in a folded state. Following appropriate intravascular positioning of the catheter 1 via a guide wire (see FIG. 2c), the filter sail arrangement 17 can be unfolded sequentially by withdrawing the hollow catheter 20 relative to the wire 20 with the filter sail arrangement 17 mounted thereon on account of the shape-memory effect inherent to the filter sail material. That is the distal-end, smaller filter sail 17" unfolds first and nestles via its umbrella-like peripheral edge against the inner wall 9 of the bodily vessel. As a result of further withdrawal, the slightly larger filter sail 17' also unfolds at a distance from the smaller filter sail 17". In the unfolded state of both sails, which each nestle against the vessel inner wall 9, it is ensured that no ablated thrombus material can travel around in the bodily vessel in an uncontrolled manner, since all tissue material separated from the vessel inner wall 9 is either aspirated through the opened separating gap 3 of the catheter 1 or is caught by the filter sail arrangement 17. On the other hand, both braced filter sails 17" and 17' ensure the holding torque or counter-torque providing support with respect to the vessel inner wall 9 and necessary for the influence of the torque along the catheter 1 in order to open the helically winding separating gap 3.

Figure 2E:
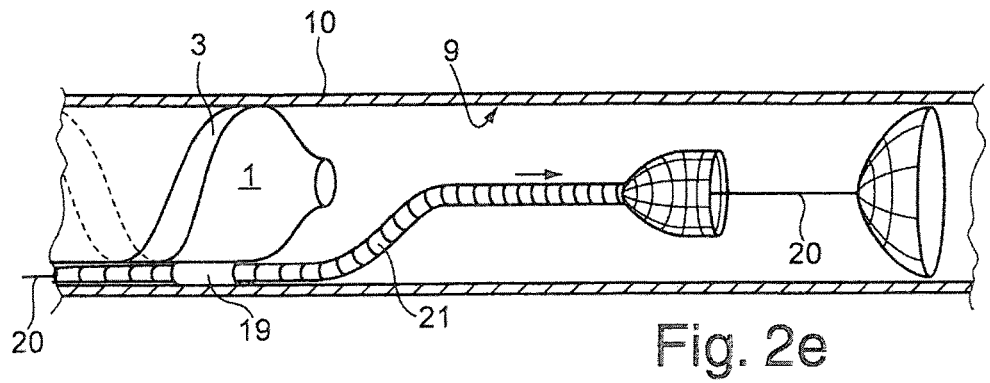

Once the tissue has been removed, the catheter 21 is slid forwards distally relative to the wire 20, whereby the catheter 21 initially slides over the larger filter sail and folds this in the manner of an umbrella as shown in FIG. 2e. Here, all tissue particles caught by the filter sail 17' are detained reliably inside the catheter 21. By sliding the catheter 21 further forwards, the smaller filter sail 17" is stowed in the same way within the catheter 21.

The catheter 1 in all conceivable embodiments also has, for the purpose of a facilitated intracorporeal navigation of the catheter, at least one radiopaque marking 7, on the basis of which an operator can monitor the exact position of the catheter 1 with the aid of suitable X-ray monitoring methods. Two radiopaque markings 7 and 7' (see FIG. 4a) which preferably define, distally and proximally, the catheter region 2 along which the helically winding separating gap 3 is formed. As a result, an operator is always aware of the intracorporeal position of the entire catheter section 2 during the intervention.

Figure 3:
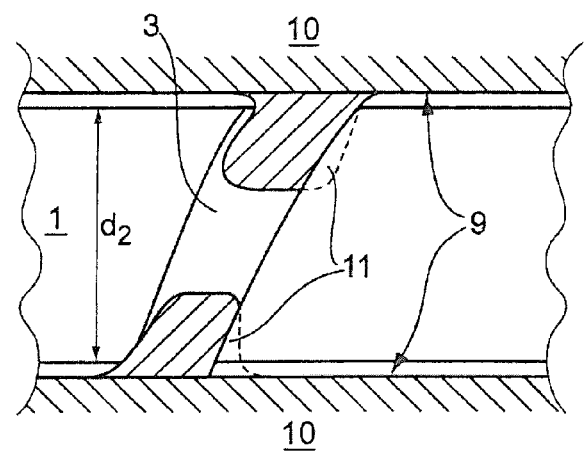
FIG. 3 shows a catheter section placed within a hollow vessel opposite a thrombus.

Following appropriate positioning and anchoring of the catheter 1 within the hollow vessel, the catheter 1 must be opened along its helically winding separating gap 3. To this end, an operator exerts a torque D having a direction of rotation oriented against the winding direction of the helically winding separating gap 3 onto the catheter 1 from the proximal end of the catheter, either manually or with the aid of a suitable rotating device 8 (see FIG. 1a). Due to the separating gap opening, the catheter outer diameter $d_2$ also enlarges uniformly along the catheter as illustrated in FIG. 3 at the same time and nestles under application of a compressive force against the inner wall 9 of a hollow vessel 10 as seen in FIG. 3. Parietal thrombus material 11 can now infiltrate into the opened separating gap 3. This process of the infiltration of thrombus material through the splayed separating gap 3 into the lumen of the catheter 1 can be assisted advantageously by application of an aspiration vacuum along the catheter lumen. To this end, the catheter 1 has in the proximal region a fluid-tight connection structure for the application of a suitable vacuum source 12 as seen in FIG. 1a.

Following corresponding removal of the torque D, the separating gap 3 shown in FIG. 3 in the opened state closes and at the same time the separated cutting edges of the faces of the splayed separating gap 3 shear off thrombus material 11, which remains on the inner wall 9 and reaches into the interior of the catheter 1, from the inner wall 9 of the hollow vessel 10. As a result of removal in the proximal direction, the thrombus material can thus be reliably brought outside the body in the interior of the catheter.

Figure 4A:
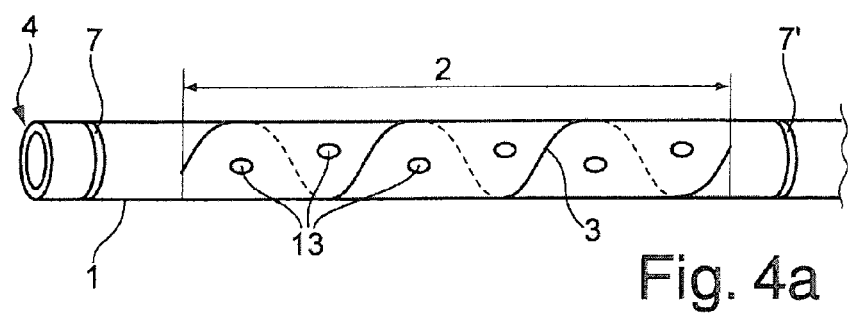
FIGS. 4a and b show schematic illustrations of a further embodiment of a catheter formed in accordance with the invention a) in a state free from external forces and b) with a torque acting along the catheter.
Figure 4B:
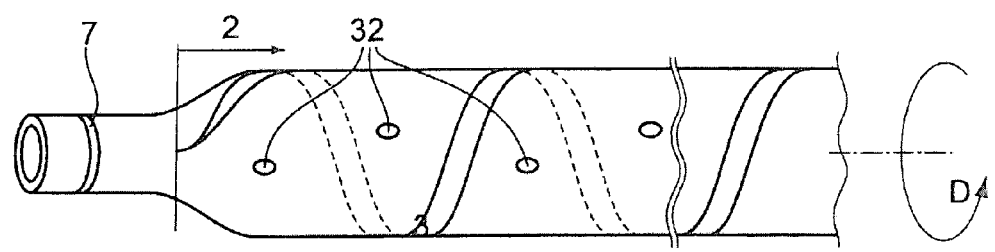

FIGS. 4a and b show a further alternative exemplary embodiment for forming the catheter 1 according to the invention, which, in addition to the helically winding separating gap 3 along the catheter section 2, have wall openings 13 passing completely through the catheter wall 3 and in contrast to the separating gap 3, are formed in the catheter wall by way of a material-removing procedure, as for example by a punching procedure, or a mechanical or thermal material-removing abrasive procedure. The wall openings 13 retain their opening geometry in an unaltered manner irrespective of the resilient change in shape of the catheter 1 and, in conjunction with a vacuum application in the interior of the catheter 1, enable additional possibilities for the safe ablation and reliable storage of separated parietal thrombus material in the interior of the catheter 1.

The dimensions of the catheter 1 according to the invention are dependent on the geometric conditions of intracorporeal hollow vessels. The axial length of the catheter section 2 along which the least one helically winding separating gap 3 is provided thus measures approximately between 1 cm and 1 m. Of course, it is possible to form one or more helically winding separating gaps along the catheter 1 in different axial regions, which are separated axially from one another.

Suitable catheter outer diameters that the catheter assumes in a torque-free state are typically between 1 mm and 25 mm, wherein the catheter has a catheter wall thickness between 0.1 mm and 2.5 mm. In the case of the torque-induced widening of the catheter, the opened separating gap typically has gap widths between 0.1 mm and 50 mm, preferably between 0.5 mm and 10 mm. The additional wall openings 13 illustrated in FIGS. 4a and b typically have opening widths from 0.1 mm to 20 mm.

The catheter 1 according to the invention, for the purpose of the ablation of parietal thrombus material deposits, therefore does not require any cutting tools to be handled in addition to the catheter or any displacement bodies radially widening the catheter. Instead the catheter in accordance with the invention is fixed intravasally and is to be subjected exclusively to a torque, as a result of which the catheter deploys its full functionality.

LIST OF REFERENCE SIGNS 1 catheter
2 catheter section
3 helically winding separating gap
31 turn
32, 33 sectional faces
4 distal catheter end
5 balloon
6 balloon catheter
7, 7' radiopaque marking
8 rotary motor
9 vessel inner wall
10 hollow vessel
11 thrombus material
12 vacuum source
13 wall opening
14 additional lumen
15 stent
16 guide wire
17 filter sail arrangement
17', 17" filter sail
18 connection
19 additional lumen
20 wire
21 catheter

The invention claimed is:

1. A device for detaching a parietal thrombus from a body vessel comprising:
a catheter including at least one catheter section disposed longitudinally relative to the catheter;
a catheter wall including at least one wall opening passing completely through the catheter wall;
the catheter wall being disposed longitudinally relative to the least one catheter section and comprising a resiliently deformable material, the at least one wall opening including a separating gap wound helically with a constant pitch around the catheter wall at least in parts of the at least one catheter section including a cut passing completely through the catheter wall having two faces which include cutting edges that contact each other when the separating gap is closed, the catheter in a distal direction from the separating gap including a fixing device configured for releasably fixing the catheter to the body vessel;
means configured for severing at least part of the parietal thrombus from the body vessel including the cutting edges which are responsive to removal of torque acting on the catheter when the parietal thrombus is at least partially within the opening to sever the at least part of the parietal thrombus;
the catheter being configured so that torque acting on the catheter causes diameter of the catheter to expand from a smaller catheter outer diameter when the faces including the cutting edges contact each other to a larger catheter outer diameter which is constant along the catheter and causes the separating gap to change from being closed to being opened with the faces including the cutting edges being separated; and
the catheter, in an absence of an external constraint being applied thereto while the parietal thrombus is at least partially within the opening, is configured to spontaneously adopt the smaller catheter outer diameter due to resilient restoring forces of the resiliently deformable material causing the separating gap to close to activate the means configured for severing to cause the cutting edges to sever at least part of the parietal thrombus from the body when the parietal thrombus is at least partially within the opening; and wherein
the fixing device comprises a dilatable balloon mounted on the catheter and is either spaced distally from the separating gap or is positioned distally from the catheter, and the balloon is inflatable by a lumen which is disposed along the lumen.

2. The device according to claim 1, wherein the catheter comprises an inner catheter lumen, the at least one catheter section is tubular, and the resiliently deformable material is an elastomer.

3. The device according to claim 2, wherein the elastomer is made of at least one material selected from:

poly(methyl methacrylate) (PMMA), polytetrafluoroethylene (PTFE), polyurethanes, polyether urethanes, silicone polyether urethanes, silicone polyurethanes, silicone polycarbonate urethanes, polyolefin elastomers, polyisobutylenes, fluorosilicones, polyvinyl chloride (PVC), polydimethylsiloxane (PDMS), polylactides, polyethylene, polybutylmethacrylate, polyacrylamide, polyacrylonitriles, polyamides, polyetheramides, polyethylene amine, polyimides, polycarbonates, polycarbonate urethanes, polyvinyl ketones, polyvinyl halides, polyvinylidene halides, polyvinyl ether, polyisobutylenes, polyvinyl aromates, polyvinyl ester, polyvinyl pyrrolidones, polyoxymethylenes, polytetramethylene oxide, nylon or polyester.

4. The device according to claim 1 wherein:
the at least one catheter section ranges from 1 cm to 100 cm in length, has a resilient section having a catheter outer diameter ranging from 1 mm to 25 mm and the catheter wall ranges in thickness, without influence of the external constraint to between 0.1 mm and 2.5 mm.

5. The device according to claim 1, wherein:
the separating gap along the at least one catheter section has at least one helical turn.

6. The device according to claim 1 wherein:
the catheter extends longitudinally, includes at least one first catheter section and includes a second catheter section which is axially separated from the at least one first catheter section, and the separating gap is formed in at least two catheter sections each wound in an identical winding direction.

7. The device according to claim 1, wherein:
the balloon is positioned inside a radially flexible stent which when the balloon is inflated the balloon is configured to contact a stent which is configured to radially expanded and contact an inner wall of the vessel.

8. The device according to claim 1 wherein:
the catheter at a proximal end includes a connector to which a vacuum source is attachable.

9. The device according to claim 1 comprising:
at least one radiopaque marking is mounted in a region of a catheter tip associated with at least one of the catheter and along the at least one catheter section.

10. The device according to claim 1 wherein:
the sectional faces of the cut are separated by the external constraint when the catheter is converted from the smaller outer diameter to the larger outer diameter and encloses the separation gap which has a pitch that is larger than a pitch associated with the separation gap when the catheter has the smaller outer diameter.

11. The device according to claim 10, wherein:
in the separation gap has a gap of a width b ranging from 0.1 mm≤b≤50 mm or 0.5 mm≤b≤10 mm.

12. The device according to claim 11, wherein in the at least one further wall opening includes a material cutout from a wall of the catheter and has a largest opening width ranging from 0.1 mm to 20 mm.

13. The device according to claim 1 comprising:
at least one further wall opening passing completely through the catheter wall along the at least one catheter section and the separating gap.

14. The device according to claim 1 wherein:
when the torque is removed, the means configured for severing comprises the faces which close and are configured to contact the parietal thrombus and sever the parietal thrombus from the vessel.

* * * * *